(12) United States Patent
Phillips

(10) Patent No.: US 8,440,239 B2
(45) Date of Patent: May 14, 2013

(54) FORMULATIONS AND TREATMENTS FOR TRICHOLOGY

(75) Inventor: Jon Phillips, Noosa Heads (AU)

(73) Assignee: Dolphst Pty Ltd., Noosa Head (QLD) (AU)

(*) Notice: Subject to any disclaimer, the term of this patent is extended or adjusted under 35 U.S.C. 154(b) by 0 days.

(21) Appl. No.: 13/008,269

(22) Filed: Jan. 18, 2011

(65) Prior Publication Data

US 2012/0020982 A1    Jan. 26, 2012

Related U.S. Application Data

(63) Continuation of application No. 11/793,748, filed as application No. PCT/AU2005/001924 on Dec. 20, 2005, now abandoned.

(30) Foreign Application Priority Data

Dec. 24, 2004  (AU) .................................. 2004907338

(51) Int. Cl.
*A61K 36/00*     (2006.01)
*A61K 36/704*   (2006.01)
*A61K 36/258*   (2006.01)

(52) U.S. Cl.
USPC ......... 424/725; 424/157.1; 424/752; 424/728

(58) Field of Classification Search ........................ None
See application file for complete search history.

(56) References Cited

U.S. PATENT DOCUMENTS

| | | | |
|---|---|---|---|
| 5,043,162 A | 8/1991 | Trager | |
| 6,149,933 A | 11/2000 | Nelson | |
| 2002/0028257 A1 | 3/2002 | Catalfo et al. | |
| 2002/0150547 A1* | 10/2002 | Lee et al. ..................... | 424/74 |
| 2002/0155085 A1 | 10/2002 | Kamimura et al. | |
| 2003/0028169 A1* | 2/2003 | Fossel ........................ | 604/500 |
| 2003/0104079 A1 | 6/2003 | Sakanaka et al. | |
| 2004/0096420 A1 | 5/2004 | Catalfo et al. | |
| 2004/0213859 A1* | 10/2004 | Zelickson ................... | 424/725 |

FOREIGN PATENT DOCUMENTS

| | | |
|---|---|---|
| DE | 1617532 | 4/1971 |
| EP | 1175887 | 2/2012 |
| FR | 2854066 | 10/2004 |
| GB | 2240715 | 8/1991 |
| JP | 63-154604 | 6/1988 |
| JP | 02006403 | 1/1990 |
| JP | 02006403 A * | 1/1990 |
| JP | 03-133918 | 6/1991 |
| JP | 08-073325 | 3/1996 |
| JP | 09-241135 | 9/1997 |
| JP | 10-279441 | 10/1998 |
| JP | 2000-044439 | 2/2000 |
| JP | 2000302678 | 10/2000 |
| JP | 2000351715 | 12/2000 |
| JP | 2008291025 | 12/2008 |
| WO | WO 94/05250 | * 3/1994 |
| WO | WO9405250 | 3/1994 |
| WO | WO9801167 | 1/1998 |
| WO | WO 98/36759 | * 8/1998 |
| WO | WO9836759 | 8/1998 |
| WO | WO2004039454 | 5/2004 |
| WO | WO2006073457 | 7/2006 |

OTHER PUBLICATIONS

Lowe et al, Zinc source influences zinc retention in hair and hair growth in the dog, Journal of Nutrition (1994), 124(12S), 2575S-6S.*
Amichai B. et al; International Journal of Dermatology, "5α-reductase inhibitors—a new hope in dermatology?" 1997, 36: 182-184.
Brzesinska-Wcislo L.; "Evaluation of vitamin B6 and calcium pantothenate effectiveness on hair growth from clinical and trichographic aspects for treatment of diffuse alopecia in women"; 2001; Wiadomosci Lekarskie, Fundacja Lekarzy Polskich, Warsaw, PL, 54 (1-2): 11-18.
Haber, R.S.; Facial Plastic Surgery Clinical North America; "Pharmacologic management of pattern hair loss"; 12: 181-189, 2004.
Hair Loss Formula; http://web.archive.org/web/20041010185956/http://www.multiflora.co.uk/hairlossformula; Oct. 10, 2004.
Horsetail; http://web.archive.org/web/20040722082531/http://www.rain-tree.com/horsetail.htm; Jul. 22, 2004.
Kobayashi N et al.; Journal of the Pharmaceutical Society of Japan; "Effect of Leaves of *Ginkgo biloba* on Hair Regrowth in C3H Strain Mice" 113(10); 718-724; 1993.
Kvedar J C et al, American Journal of Medical Genetics, "Dietary Management Reverses Grooving and Abnormal Polarization of Hair Shafts in Argininosuccinase Deficiency"; 40(2): 211-213; 1991.
Learn About Hair Loss, HTTP://web.archive.org/web/*/http://endhairlossnatually.com/hair.loss.ingredients.DHT.htm; Jun. 5, 2004.
Multiples/Formulas: Hair vitamins retrieved Oct. 11, 2004; http://web.archive.org/web/20041011201116/http://www.vitaminlab.com/product.cfm?selected_items=55390&HAIR-VITAMINS.
Simon HB: "Hair Loss: Telling the Bald Truth"; Newsweek, 24:77, 2003.
Lowe et al.; "Zinc Source Influences Zinc Retention in Hair and Hair Growth in the Dog"; Journal of Nutrition (1994), 124(12S), 2575S-6S.
Wen et al.; "Ginseng Root Prevents Learning Disability and Neuronal Loss in Gerbils With 5-Minute Forebran Ischemia"; Acta Neuropathol (1996) 91: 15-22.

* cited by examiner

*Primary Examiner* — Qiuwen Mi
(74) *Attorney, Agent, or Firm* — Abelman, Frayne & Schwab

(57) ABSTRACT

A formulation for trichological treatment of a patient including, in a dosage in the range of 3 g to 8 g: phytosterols in the range of 200 mg to 2500 mg; the quantitative equivalent of *Polygonum multiflorum* root 4:1 in 70% EW in the range of 600 mg to 2600 mg; methylsulfonylmethane in the range of 500 mg to 2000 mg; and bovine colostrum in the range of 500 m to 2000 m.

2 Claims, No Drawings

FORMULATIONS AND TREATMENTS FOR TRICHOLOGY

CROSS-REFERENCE TO RELATED APPLICATIONS

This application is a continuation of U.S. application Ser. No. 11/793,748, (now abandoned) filed Jun. 20, 2007, which is a National Phase of PCT/AU2005/001924, filed Dec. 20, 2005, which claims priority from Australian Application No. 2004/907338, filed Dec. 24, 2004, all of which are incorporated herein by reference.

FIELD OF INVENTION

This invention relates to formulations and treatments for trichology. The invention is primarily directed to formulations and treatments for reduction of hair loss and/or hair regrowth typically exhibited in adult humans having a condition sometimes referred to alopecia. Although the condition is more prevalent in human males and is sometimes referred to as male pattern alopecia, the invention is applicable to treatment of both male and female alopecia.

BACKGROUND ART

Herbal extracts and formulations have been suggested for the trichological treatment of humans, particularly males, but not exclusively so. Efficacy varies from nil to some reduction in hair loss and/or noticeable hair regrowth on the heads of patients. However, the interaction of the constituent compounds in such formulations with one another is little understood. The respective modes of action of such formulations are quite diverse. Generally, such treatments are either topical or systemic.

The term alopecia is used in the art generally to refer to all conditions of baldness, including partial baldness, and the term alopecia is used in this specification to have the same meaning, as well as to refer to hair loss generally, unless the context requires otherwise. The term "trichological treatment" is used to refer to the treatment and/or formulations for the treatment of alopecia and hair thinning in males and females. Although the term is used sometimes to refer to scalp conditions or the like, the invention is not limited to treatment of such conditions, and may be used to treat hair loss on other parts of the body.

There are several root causes of alopecia, some of which are well established both clinically and pathologically, and quite well understood. Other root causes are not well understood and/or subject of conjecture. Some herbal and drug treatments of alopecia are directed to one or more of the root causes of alopecia, whether they be well understood or merely conjectured. There is a quantity of research data on efficacy, some of which is in conflict, indicating that the alopecia condition is complex, and is probably affected by a range of different mechanisms. Some root causes are expressed or exhibited more than others, but unless several of such root causes are addressed by a proposed remedy, it is suggested that its efficacy may be limited.

The present invention aims to provide formulations and treatments for trichology which alleviate one or more of the shortcomings of the prior art. Other aims and advantages of the invention may become apparent from the following description.

DISCLOSURE OF THE INVENTION

With the foregoing in view, this invention in a first aspect resides broadly in a formulation for trichological treatment including a 5-alpha reductase production inhibitor and methylsulfonylmethane.

In a second aspect, the present invention resides broadly in a formulation for trichological treatment including:
 a 5-alpha reductase production inhibitor;
 methylsulfonylmethane; and
 extract from the herbal variety *Polygonum multiflorum*.

In a third aspect, the present invention resides broadly in the present invention resides broadly in a formulation for trichological treatment including:
 a 5-alpha reductase production inhibitor;
 methylsulfonylmethane;
 extract from the herbal variety *Polygonum multiflorum*; and
 colostrum.

In a fourth aspect, the present invention resides broadly in the present invention resides broadly in a formulation for trichological treatment including:
 a 5-alpha reductase production inhibitor;
 methylsulfonylmethane;
 extract from the herbal variety *Polygonum multiflorum*; and
 levo-arginine.

In a fifth aspect, the present invention resides broadly in the present invention resides broadly in a formulation for trichological treatment including:
 a 5-alpha reductase production inhibitor;
 methylsulfonylmethane;
 extract from the herbal variety *Polygonum multiflorum;*
 levo-arginine and
 colostrum.

In a sixth aspect, the present invention resides broadly in the present invention resides broadly in a formulation for trichological treatment including:
 a 5-alpha reductase production inhibitor;
 methylsulfonylmethane;
 extract from the herbal variety *Polygonum multiflorum;*
 levo-arginine;
 colostrum; and
 *Gingko biloba*.

In a seventh aspect, the present invention resides broadly in a formulation for trichological treatment including:
 extract from the herbal variety *Polygonum multiflorum;*
 a 5-alpha reductase production inhibitor;
 methylsulfonylmethane; and
 colostrum.

Preferably, the formulation includes zinc amino acid chelate. Preferably the formulation includes *Gingko biloba*. More preferably, the formulation includes both zinc amino acid chelate and *Gingko biloba*. It is further preferred that the formulation includes any one or more extracts from the herbal varieties:
 *Polygonum multiflorum;*
 *Gingko biloba;*
 *Equisetum arvense;*
 *Panax quinquefolium*.

It is further preferred that the formulation includes any one or more of the following components:
 one or more soy isoflavones;
 levo-arginine;
 inositol;
 niacin;
 biotin;

calcium pantothenate;
dextro-alpha-tocopherol;
Pyridoxine hydrochloride;

Preferably, the colostrum is bovine colostrum. However, it will be appreciated that other mammalian sources of colostrum may be used, particularly colostrum which are efficacious in ameliorating the reduction of growth hormone ("GH") and/or insulin-like growth factor 1 ("IGF-1") with ageing. Preferably, the components are provided in relative quantities selected to provide efficacy in respect of their known functional qualities. Preferably, the 5-alpha reductase production inhibitor is selected from one or more phytosterols, particularly, as equivalents to beta-sitosterol. Alternatively, or in addition thereto, the 5-alpha reductase production may inhibitor may include extract from *Serena repens*, or Saw palmetto. The herbal extracts may also include *Pygeum repens*. The formulation may also include thiamine. The formulation may also include riboflavin.

In an eighth aspect, the present invention resides broadly in a formulation for trichological treatment of a patient including, in a dosage in the range of 3 g to 8 g:
phytosterols in the range of 200 mg to 2500 mg;
the quantitative equivalent of *Polygonum multiflorum* root 4:1 in 70% EW in the range of 600 mg to 2600 mg;
methylsulfonylmethane in the range of 500 mg to 2000 mg; and bovine colostrum in the range of 500 mg to 2000 mg.

Preferably, the formulation further includes the quantitative equivalent of *Gingko biloba* leaf extract 50:1 in 70% EW in the range of 50 mg to 1000 mg. Preferably, the formulation further includes the quantitative equivalent of zinc amino acid chelate 20% in the range of 10 mg to 40 mg. More preferably, the formulation includes both the *Gingko biloba* and the zinc amino acid chelate. It is also preferred that the formulation includes any one or more of the following components:
arginine in the range of 120 mg to 500 mg;
biotin in the range of 0.7 mg to 5 mg;
nicotinic acid in the range of 5 mg to 30 mg;
calcium pantothenate in the range of 10 mg to 400 mg;
pyridoxine hydrochloride in the range of 10 mg to 400 mg;
d-α-tocopherol acetate in the range of 200 IU to 800 IU; and
colloidal anhydrous silica in the range of 60 mg to 500 mg.

It is also preferred that the formulation also include any one or more of the following components:
the quantitative equivalent of *Glycine Max* (soy) seed 65:1 in 75% EW in the range of 80 mg to 3250 mg;
the quantitative equivalent of *Panax quinquefolium* root extract 3:1 in 15% EW in the range of 50 mg to 1000 mg;
the quantitative equivalent of *Equisetum arvense* herb extract 4:1 in 100% water in the range of 50 mg to 1000 mg;
inositol in the range of 70 mg to 300 mg;

Preferably, the phytosterols are in the range of 200 mg to 2500 mg. More preferably, the phytosterols are in the range of 200 mg to 1000 mg. Preferably, the *Gingko biloba* extract is in the range of 50 mg to 1000 mg. More preferably, the *Gingko biloba* extract is in the range of 50 mg to 500 mg. Preferably, the *Panax quinquefolium* root extract is in the range of 50 mg to 1000 mg. More preferably, the *Panax quinquefolium* root extract is in the range of 50 mg to 500 mg. Preferably, the *Equisetum arvense* herb extract is in the range of 50 mg to 1000 mg. More preferably, the *Equisetum arvense* herb extract is in the range of 50 mg to 500 mg. Preferably, the bovine colostrum is in the range of 50 mg to 2000 mg. More preferably, the bovine colostrum is in the range of 500 mg to 1000 mg. Preferably, the biotin is in the range of 0.7 mg to 3 mg. Preferably, the pyridoxine hydrochloride is in the range of 100 mg to 400 mg. Trusil natural lemon/lime in the range of 6 to 26 mg or a flavouring agent equivalent thereto may also be added to the formulation. Fructose in the range of 125 mg to 500 mg or a sweetening agent equivalent thereto may also be added to the formulation.

In a ninth aspect, the present invention resides broadly in a formulation for trichological treatment of a patient including:
a for promoting the anagenic phase of hair growth and/or minimising the catagenic and/or telegenic phases of hair growth;
a biological sulfur nutritional supplement for providing biologically active sulfur;
one or more dihydrotestosterone blocking components for inhibiting the binding of dihydrotestosterone to receptor sites and/or inhibits the action of 5-alpha-reductase in converting testosterone to dihydrotestosterone;
one or more capillary blood-flow promoters for promoting capillary blood flow;
a growth factor component for promoting cell growth by ameliorating the reduction of growth hormone ("GH") and/or insulin-like growth factor 1 ("IGF-1") with ageing;
an amino acid component having at least some of all of the essential amino acids for human metabolism; and
a mineral component for introducing at least the minerals silicon and zinc into the patient.

Preferably, the formulation includes a vitamin component having at least some vitamin B1, vitamin B2, vitamin B3, vitamin B5, vitamin B8, vitamin $B_x$, and vitamin E.

Preferably, the components are selected from the phytosterols, *Polygonum multiflorum* root, *Glycine Max* (soy) seed, *Gingko biloba* leaf, *Panax quinquefolium* root, *Equisetum arvense*, inositol, methylsulfonylmethane, bovine colostrum, arginine, biotin, nicotinic acid, calcium pantothenate, pyridoxine hydrochloride, d-α-tocopherol acetate, Trusil natural lemon/lime or a flavouring agent equivalent thereto, fructose or a sweetening agent equivalent thereto, colloidal anhydrous silica and zinc amino acid chelate to make up a dosage in the range of 2 g to 10 g as set forth in the eighth second aspect of the invention described herein.

In a tenth aspect, the present invention resides broadly in a method of treatment of hair loss in humans including the steps of:
preparing a first formulation for topical application to at least some of the skin of a human patient, the first formulation consisting of: extract from the herbal variety *Polygonum multiflorum*, methyl sulfonyl methane; a 5-alpha reductase production inhibitor; and colostrum;
preparing a second formulation for ingestion by the human patient, the second formulation consisting of: extracts from the herbal varieties of *Polygonum multiflorum*, phytosterols, *Gingko biloba*, *Equisetum arvense* and *Panax quinquefolium*; methylsulfonylmethane; soy isoflavones; levo-arginine; inositol; biotin; niacin; calcium pantothenate; dextro-alpha-tocopherol; pyridoxine hydrochloride; zinc amino acid chelate and colostrum.

Preferably, the first formulation further includes one or more of the components: methylsulfonylmethane; *Polygonum multiflorum* (fo-ti root); grape seed oil; hawthorne herb; colostrum; beta sitosterol; primrose oil; flaxseed oil; cayenne pepper; L-arginine; silica; *Gingko biloba* leaf extract and zinc sulfate, in relative quantities selected to provide efficacy in respect of their known functional qualities.

The formulations so prepared are then used in the manner suggested above in that the first formulation is applied to the skin, typically the scalp, of the patient and in close time proximity to such application, the second formulation is ingested by the patient. Typically, a dosage in the range of 2 to 8 g is efficacious. More preferably, the dosage is in the range of 5 to 6 g.

In an eleventh aspect, the present invention resides broadly in a method of treatment of hair loss in humans including the steps of:

preparing a predetermined quantity of a first formulation for systemic use, the first formulation consisting of: a hair growth component for promoting the anagenic phase of hair growth and/or minimising the catagenic and/or telegenic phases of hair growth; a biological sulfur nutritional supplement for providing biologically active sulfur; one or more dihydrotestosterone blocking components for inhibiting the binding of dihydrotestosterone to receptor sites and/or inhibiting the action of 5-alpha-reductase in converting testosterone to dihydrotestosterone; one or more capillary blood-flow promoters for promoting capillary blood flow; a growth factor component for promoting cell growth by ameliorating the reduction of growth hormone ("GH") and/or insulin-like growth factor 1 ("IGF-1") with ageing; an amino acid component having at least some of all of the essential amino acids for human metabolism; a mineral component for introducing at least the minerals silicon and zinc into the patient; and a vitamin component having at least some vitamin B1, vitamin B2, vitamin B3, vitamin B5, vitamin B8, vitamin $B_x$, and vitamin E;

preparing a predetermined quantity of a second formulation for topical application, the second formulation consisting of: a hair growth component for promoting the anagenic phase of hair growth and/or minimising the catagenic and/or telegenic phases of hair growth; a hair growth component complement for complementing the functional qualities of the hair growth component; a metabolism-balancing component for balancing the metabolism of the patient; a 5-alpha reductase production inhibitor for inhibiting the patient's production of 5-alpha reductase; an amino acid complement providing substantially all of the amino acids required for metabolism of the patient; a nitric oxide metabolite from which nitric oxide may be produced in the metabolic processes of the patient; a keratinocyte cell supplement for supplementing nutrients for the patient's keratinocyte cells; a carbohydrate metabolism facilitator for facilitating carbohydrate metabolism of the patient; a hair cortex elasticity component for enhancing the elasticity of the hair cortices of the patient; an enzymatic antioxidant and detoxifying component for detoxifying the patient, including the scavenging of oxidants; a mineral anti-oxidant component for supplementing the enzymatic antioxidant and detoxifying component; and an immunoglobulin and growth-factor supplement for supplementing the patient's intake of immunoglobulin and growth factor.

Preferably, the hair growth component includes a herbal extract from *Polygonum multiflorum*. Preferably, the hair growth complement is in the form of a sulfur metabolite such as dimethyl sulfone (methylsulfonylmethane). Preferably, the blood flow enhancement component includes a herbal extract of *Gingko biloba*. Preferably, the silica metabolite includes a herbal extract of Equisetum arvense. Preferably, the metabolism-balancing component for balancing the metabolism of the patient includes a herbal extract of *Panax quinquefolium* (American ginseng). The metabolism-balancing component preferably includes efficacy in normalising system levels in the body. American ginseng has been used to stimulate the immune system, lower cholesterol and increase energy levels. The 5-alpha reductase production inhibitor may include a herbal extract of *Serenoa repens* (Saw Palmetto) or more preferably, phytosterols (equivalent to beta-sitosterol). Preferably, the amino acid complement has substantially all of the amino acid essential for human metabolism. For example, a preferred amino acid complement includes soy isoflavones. Preferably, the nitric oxide metabolite includes 1-arginine. Preferably, the keratinocyte cell supplement includes inositol. Preferably, the carbohydrate metabolism facilitator for facilitating carbohydrate metabolism of the patient includes niacin. It is believed that niacin is essential for the metabolism of carbohydrate. Preferably, the hair cortex elasticity component includes biotin. More preferably, the biotin and niacin, being part of the vitamin B-complex family, are included with other vitamin B-complex vitamins, such as riboflavin, pantothenic acid and the like. Preferably, pantothenic acid is positively included in the second formulation in the form of a calcium salt. It is also preferred pyridoxine hydrochloride (vitamin B6) be included with the B-complex vitamins. Preferably, the enzymatic antioxidant and detoxifying component includes dextro-alpha-tocopherol (vitamin E). Preferably, the mineral anti-oxidant component includes zinc, more preferably zinc amino acid chelate. Preferably, the immunoglobulin and growth-factor supplement includes colostrum. More preferably, the immunoglobulin and growth-factor supplement includes bovine colostrum.

While the formulation has been found to have increased efficacy when used with both the topical and the systemic modes of delivery, it will be appreciated that the method of the invention is not limited to the inclusion of both modes of delivery of one or more of the formulations according to the invention.

Preferably, at least one of the capillary blood-flow promoters is functional in use to promote opening of potassium channels in cell membranes of patients. Preferably, the amino acid component includes isoflavones and/or phytosterols. More preferably, the amino acid component includes a phytoestrogen. More preferably, the amino acid component includes Genistein. In another preferred form, the amino acid component includes Daidzien. The vitamin and mineral components may be constituted from one or more sources. For example, the silicon mineral may be derived from the herb known as horsetail, Equisetum arvense. The zinc mineral may be contained in a zinc citrate or the like.

Preferably, preparation of the formulation for ingestion includes forming the components into respective component powders, mixing the component powders together and packaging the powder into predetermined dosage packs. One preferred dosage pack contains the mixed powder in the range of 3 g to 9 g powder. In a particular preferred form, the dosage is 5.5 g powder. In such form, it is preferred that the mixed powder be ingested in a drink, such as water, but it will be appreciated that a wide range of potable liquids would be suitable. It is suggested that a monthly supply of 200 g to 1000 g powder is efficacious when taken in accordance with the method of the invention. Of course, colouring and/or flavouring additives may be included, as well as dispersing and/or emulsifying agents, thickeners, preservatives or the like.

The powder may be formed so as to have different flavourings and/or colourings. Moreover, the powder may be flavoured differently for different diluents, such as, for example, a fruit-type flavour for mixing in water and a vanilla, chocolate or caramel flavour for mixing in milk or non-dairy equivalents of milk.

Preferably, the preparation of the formulation for topical application includes forming the components into respective component powders, mixing the component powders together and mixing, folding, blending or combining the powders into a paste formed with liquid, such as oil, water or such like to such consistency that it can be delivered through an eye-dropper. In a particular preferred form, the dosage is 0.5 to 5 ml per application. For example, a paste may be prepared using alcohol as a diluent. Other oils, water and/or emulsifying agents may also used in addition to or instead of the alcohol. It is suggested that the mixture be formed into a flowable material of such consistency that it can flow through an eye-dropper.

In a twelfth aspect, the present invention resides broadly in a serum formulation for trichological treatment of a patient including: methylsulfonylmethane; *Polygonum multiflorum* (fo-ti root); one or more plant and/or seed oils; hawthorne herb; colostrum; beta sitosterol; cayenne pepper; L-arginine; *Gingko biloba* leaf extract and zinc sulfate, in relative quantities selected to provide efficacy in respect of their known functional qualities. Preferably, the serum includes silica. Preferably, the one or more plant and/or seed oils include any one, two or all of the group selected from grape seed oil, primrose oil and flaxseed oil.

In a thirteenth aspect, the present invention resides broadly in a medicinal formulation for trichological treatment including:

extracts from the herbal varieties:
*Polygonum multiflorum;*
*Gingko biloba;*
*Equisetum arvense;*
*Panax quinquefolium;*
methylsulfonylmethane;
levo-arginine;
a 5-alpha reductase production inhibitor;
one or more soy isoflavones;
inositol;
niacin;
biotin;
calcium pantothenate;
dextro-alpha-tocopherol;
Pyridoxine hydrochloride;
zinc amino acid chelate; and
colostrum.

The constituents of the medicinal formulation are preferably selected in substantially in accordance the limitations of corresponding constituents of the other corresponding aspects of the invention as herein described.

BRIEF DESCRIPTION OF THE EXAMPLES

In order that the invention may be more readily understood and put into practical effect, reference will now be made to one or more examples of the invention wherein at least some of the aspects and embodiments of the invention are described from experimental work in the development of the invention.

DETAILED DESCRIPTION OF THE EXAMPLES

Example 1

A batch of material was formulated according to the details set forth in Table 1 below.

| Ingredient (and Strength) | Label Claim | mg | mg/dose | overage | mg per g (including overage) | weight for mix (kg) |
|---|---|---|---|---|---|---|
| phytosterols (equiv. B-sitosterol 33%) | 500.00 | 303 | 1515 | 3% | 312.09 | 35.344 |

-continued

| Ingredient (and Strength) | Label Claim | mg | mg/dose | overage | mg per g (including overage) | weight for mix (kg) |
|---|---|---|---|---|---|---|
| Polygonum multiflorum (fo ti) root 4:1 in 70% EW | 1350.00 | 67.5 | 337.5 | 5% | 70.88 | 8.027 |
| Glycine max (soy) seed 65:1 in 75% EW | 1625.00 | 5 | 25 | 0% | 5.00 | 0.566 |
| Gingko biloba leaf ext (50:1 in 70% EW) | 100.00 | 0.04 | 2 | 5% | 0.42 | 0.048 |
| Panax quinquefolium root ext (3:1 in 15% EW) | 100.05 | 6.67 | 33.35 | 5% | 7.00 | 0.793 |
| Equisetum arvense herb ext (horsetail) (4:1 in 100% water) | 100.0 | 5 | 25 | 5% | 5.25 | 0.595 |
| inositol | 150.00 | 30 | 150 | 5% | 31.50 | 3.567 |
| methyl-sulfonyl-methane (MSM) | 1000.00 | 200 | 1000 | 5% | 210.00 | 23.783 |
| colostrum (bovine) | 1000.00 | 200 | 1000 | 5% | 310.00 | 23.783 |
| arginine | 250.00 | 50 | 250 | 0% | 50.00 | 5.663 |
| biotin | 1.40 | 0.28 | 1.4 | 5% | 0.29 | 0.033 |
| nicotic acid | 15.00 | 3 | 15 | 5% | 3.15 | 0.357 |
| calcium pantothenate | 200.00 | 40 | 200 | 4% | 41.67 | 4.719 |
| pyridoxine hydrochloride | 25 | 5 | 25 | 5% | 5.24 | 0.595 |
| d-α-tocopherol acetate (dry vitamin E acetate) | 400 IU | 107.2 | 536 | 5% | 112.56 | 12.747 |
| Trusil natural lemon/lime | 13 | 2.6 | 13 | 5% | 2.73 | 0.309 |
| fructose | 250 | 50 | 250 | 0% | 50.00 | 5.663 |
| silica colloidal anhydrous | 125 | 25 | 125 | 0% | 25.00 | 2.831 |
| zinc amino acid chelate 20% x | 20 | 20 | 100 | 5% | 21.00 | 2.378 |
| Total | 6804.45 | 1120.65 | 5603.25 | | | 131.799 |

The resulting formulation was tested against a placebo on a number of individuals for hair loss. The test results revealed that the formulation was efficacious in the treatment of hair loss.

Example 2

A batch of material was formulated according to the details set forth in Table below.

| INGREDIENT | LABEL CLAIM (mg per 5 g serve) | Mg | Mg/Dose |
|---|---|---|---|
| Phytosterols (Equiv B-sitosterol 33%) | 125.00 | 75.75 | 378.75 |
| Polygonum multiflorum (Fo Ti) root 4:1 in 70% EW | 337.50 | 16.88 | 84.38 |

-continued

| INGREDIENT | LABEL CLAIM (mg per 5 g serve) | Mg | Mg/Dose |
|---|---|---|---|
| Glycine Max (Soy) seed 65:1 in 75% EW | 406.25 | 1.25 | 6.25 |
| Ginkgo Biloba leaf ext (50:1 in 70% EW) | 25.00 | 0.10 | 0.50 |
| Panax quinquefolium root ext (3:1 in 15% EW) | 25.01 | 1.67 | 8.34 |
| Equisetum arvense herb Ext (Horsetail) (4:1 in 100% Water) | 25.00 | 1.25 | 6.25 |
| Inositol | 37.50 | 7.50 | 37.50 |
| Methylsulfonylmethane (MSM) | 250.00 | 50.00 | 250.00 |
| Colostrum (Bovine) | 250.00 | 50.00 | 250.00 |
| Arginine | 62.50 | 12.50 | 62.50 |
| Biotin | 0.35 | 0.07 | 0.35 |
| Nicotinic Acid | 3.75 | 0.75 | 3.75 |
| Calcium Pantothenate | 50.00 | 10.00 | 50.00 |
| Pyridoxine Hydrochloride | 6.25 | 1.25 | 6.25 |
| d-alpha tocopheryl acetate (Dry Vitamin E Acetate) | 100 IU | 26.80 | 134.00 |
| Trusil Natural Lemon/Lime | 3.25 | 0.65 | 3.25 |
| Fructose | 62.50 | 12.50 | 62.50 |
| Silica-Colloidal Anyhydrous | 31.25 | 6.25 | 31.25 |
| Zinc Amino Acid Chelate 20% | 5.00 | 5.00 | 25.00 |
| Total | 1706.11 | 280.16 | 1400.81 |

The resulting formulation was tested against a placebo on a number of individuals for hair loss. The test results revealed that the formulation was efficacious in the treatment of hair loss.

Example 3

A batch of material was formulated according to the details set forth in Table 3 below.

| INGREDIENT | LABEL CLAIM (mg per 5 g serve) | Mg | Mg/Dose |
|---|---|---|---|
| Phytosterols (Equiv B-sitosterol 33%) | 250.00 | 151.50 | 757.50 |
| Polygonum multiflorum (Fo Ti) root 4:1 in 70% EW | 675.00 | 33.75 | 168.75 |
| Glycine Max (Soy) seed 65:1 in 75% EW | 812.50 | 2.50 | 12.50 |
| Ginkgo Biloba leaf ext (50:1 in 70% EW) | 50.00 | 0.20 | 1.00 |
| Panax quinquefolium root ext (3:1 in 15% EW) | 50.03 | 3.34 | 16.68 |
| Equisetum arvense herb Ext (Horsetail) (4:1 in 100% Water) | 50.00 | 2.50 | 12.50 |
| Inositol | 75.00 | 15.00 | 75.00 |
| Methylsulfonylmethane (MSM) | 500.00 | 100.00 | 500.00 |
| Colostrum (Bovine) | 500.00 | 100.00 | 500.00 |
| Arginine | 125.00 | 25.00 | 125.00 |
| Biotin | 0.70 | 0.14 | 0.70 |
| Nicotinic Acid | 7.50 | 1.50 | 7.50 |
| Calcium Pantothenate | 100.00 | 20.00 | 100.00 |
| Pyridoxine Hydrochloride | 12.50 | 2.50 | 12.50 |
| d-alpha tocopheryl acetate (Dry Vitamin E Acetate) | 200 IU | 53.60 | 268.00 |
| Trusil Natural Lemon/Lime | 6.50 | 1.30 | 6.50 |
| Fructose | 125.00 | 25.00 | 125.00 |
| Silica-Colloidal Anyhydrous | 62.50 | 12.50 | 62.50 |
| Zinc Amino Acid Chelate 20% | 10.00 | 10.00 | 50.00 |
| Total | 3412.23 | 560.33 | 2801.63 |

The resulting formulation was tested against a placebo on a number of individuals for hair loss. The test results revealed that the formulation was efficacious in the treatment of hair loss.

Example 4

A batch of material was formulated according to the details set forth in Table 4 below.

| INGREDIENT | LABEL CLAIM (mg per 5 g serve) | Mg | Mg/Dose |
|---|---|---|---|
| Phytosterols (Equiv B-sitosterol 33%) | 1000.00 | 606.00 | 3030.00 |
| Polygonum multiflorum (Fo Ti) root 4:1 in 70% EW | 2700.00 | 135.00 | 675.00 |
| Glycine Max (Soy) seed 65:1 in 75% EW | 3250.00 | 10.00 | 50.00 |
| Ginkgo Biloba leaf ext (50:1 in 70% EW) | 200.00 | 0.80 | 4.00 |
| Panax quinquefolium root ext (3:1 in 15% EW) | 200.10 | 13.34 | 66.70 |
| Equisetum arvense herb Ext (Horsetail) (4:1 in 100% Water) | 200.00 | 10.00 | 50.00 |
| Inositol | 300.00 | 60.00 | 300.00 |
| Methylsulfonylmethane (MSM) | 2000.00 | 400.00 | 2000.00 |
| Colostrum (Bovine) | 2000.00 | 400.00 | 2000.00 |
| Arginine | 500.00 | 100.00 | 500.00 |
| Biotin | 2.80 | 0.56 | 2.80 |
| Nicotinic Acid | 30.00 | 6.00 | 30.00 |
| Calcium Pantothenate | 400.00 | 80.00 | 400.00 |
| Pyridoxine Hydrochloride | 50.00 | 10.00 | 50.00 |
| d-alpha tocopheryl acetate (Dry Vitamin E Acetate) | 800 IU | 214.40 | 1072.00 |
| Trusil Natural Lemon/Lime | 26.00 | 5.20 | 26.00 |
| Fructose | 500.00 | 100.00 | 500.00 |
| Silica-Colloidal Anyhydrous | 250.00 | 50.00 | 250.00 |
| Zinc Amino Acid Chelate 20% | 40.00 | 40.00 | 200.00 |
| Total | 13648.90 | 2241.30 | 11206.50 |

The resulting formulation was tested against a placebo on a number of individuals for hair loss. The test results revealed that the formulation was efficacious in the treatment of hair loss.

In use, the formulations and methods of the present invention may be used for the treatment of hair loss in a human patient. It is believed that the formulations of the present invention, together with the method of dual-mode treatment, contribute synergistically to provide enhanced results of greater efficacy than either the individual components or modes of treatment. It is believed that the formulation assists either in decreasing levels of dihydrotestosterone build-up or the blocking of this material at receptor sites. It is believed that the ingredients of the present invention all make a contribution to the potency of the formula. It is believed that all of the components independently have hair health benefits. The beneficial effects of the treatment are believed to include elimination, or reduction of the action of dihydrotestosterone, remediation of incorrect flow or lack of circulation both peripheral and cardiovascular, reduction of miniaturisation of the hair strand or incorrect hormonal or dietary balance.

The fo-ti-root extract component may also be known as "He Shou Wu". Its beneficial effects may be explained as follows: There are three stages of hair growth, known as the anagen stage, being the active growth phase, the catagen stage, being the regressive phase and the telegen stage, being the resting phase. For humans, normally between 50 and 100 hairs are shed everyday, whether male or female. A full head of thick hair is due to the rate of hair growth being greater or equal than the rate of fall out. That having been said, fo-ti-root prolongs the anagenic stage or growth phase, while minimising the resting or telegenic stage and catagenic or fall out stage. The Chinese herb known as Ho Shou Wu (*Polygoni multiflori* or *Radix polygoni*) also known as fo-ti-root has been demonstrated clinically to be effective in maximising hair growth stages for the benefit of hair preservation. The literal English translation for Ho Shou Wu is "black hair Mr Ho" that speaks for its ability to preserve natural hair colour, which is a further benefit of long term usage. Chinese medicine follows the belief that the condition of the hair is an indication of the body's internal systemic health. Fo-ti-root is thought to be a tonic for the endocrine glands, liver and kidneys. Fo-ti-root contains many vitamins and minerals that are vital for hair, including the b-complex vitamins, vitamin C, silicon, zinc and vitamin A.

So far as methylsulfonylmethane is concerned, prolongation of the anagenic phase of hair growth is effected when this material works to complement fo-ti-root's aforesaid functional qualities. Methylsulfonylmethane has been called "nature's beauty mineral" because it is believed to keep the hair glossy and smooth, keeps the complexion clear and youthful, and is believed to contribute to the synthesis collagen. This material is prevalent in keratin, a tough protein substance necessary for the health and maintenance for the hair, nails and skin. Some of the functional qualities of methylsufonylmethane include improved micro-circulation to the hair and scalp, maintaining structure of the proteins in the body, helping the formulation of keratin and aiding in the production of immunoglobulin. Keratin is essential for hair and nail growth and immunoglobulin maintains the immune system.

Insofar as beta sitosterol is concerned, this material can be derived for example from Saw Palmetto (*Serena Repens*), a native American member of the palm family. Saw palmetto is a source of a class of complex, chiefly unsaturated, solid alcohols widely distributed in plant an animal tissue, known as sterols. More specifically, plants contain phytosterols, or plant based sterols. Sitosterols are sterols that are found in food (sito=food). Sitosterols have been shown to slow the production of 5-alpha reductase and the binding of dihydrotestosterone to androgen receptors. Research has shown that dihyrdotestosterone is a principle cause of hair loss, and undesirable derivative of the androgenic hormone testosterone. Dihydrotestosterone floods and eventually strangles the hair follicles of genetically predisposed individuals. The key to anti-androgenic complex lies in eliminating the root cause of hair loss by blocking dihydrotestosterone at the follicle receptor site. It is believed that beta-sitosterol (stigmast-6-en-3β-ol) is a multi-site inhibitor of the formation and actions of dihydrotestosterone, inhibiting most of the binding of the dihydrotestosterone, to receptor sites, blocking the up take of dihydrotestosterone and inhibiting the action of 5-alpha-reductase, which converts testosterone to dihydrotestosterone. *Pygeum africanum* is another natural source of beta-sitosterol. Although there are some pharmaceutical substances which are used to treat hair loss and are able to block the conversion of testosterone to dihydrotestosterone, many of these have undesirable side effects including reduced sex drive and birth defects.

Insofar as ginkgo biloba is concerned, this herbal extract has a long standing tradition for use in providing natural vascular benefits when ingested or applied topically. *Gingko biloba* has been shown to protect small blood vessels and micro capillaries against loss of tone and increase in fragility. Because the action of dihydrotestosterone causes inflammation of follicle blood supply, a major factor in male and female pattern hair loss, *Gingko biloba* is beneficial and due to its functional quality of dilating blood vessels (particularly small blood vessels) and has particular ability to increase peripheral blood circulation, especially to the brain. *Gingko biloba* is believed to have beneficial effects in preventing many conditions throughout the entire body due to poor blood supply. *Gingko biloba* can also act as a powerful anti oxidant and may contribute to the oxidation of free radicals, which are believed to contribute to premature aging. Anti oxidants also protect the eyes, cardiovascular system and central nervous systems. In traditional Chinese medicine, *Gingko biloba* has been used to improve the heart and circulation. The herb has been used for many centuries by the Chinese, and has become a conventional supplement in Europe, and more recently, in the United States.

L-arginine is an amino acid, one of the building blocks of protein. However, in the present application, L-arginine serves as a precursor in the body for the production of nitric oxide, believed to have a critical role in human metabolism, and believed to be produced by the linings of the blood vessels known as the vascular endothelium. Because nitric oxide lasts only for a few seconds once produced, its discovery was particularly illusive, but once found, researchers appreciated that this was probably the mysterious molecule that controlled blood vessel dilation. L-arginine is an essential amino acid and one of the most important supplements available to improve circulation and blood vessel health. It is believed that nitric oxide causes blood vessels to relax, opening them up and promoting easy blood flow. The reason that nitric oxide is of interest in the present application, is that where hair loss and growth are concerned, vessel dilators are believed to play a role in stimulating hair growth. Nitric oxide is believed to be a critical link in the hair growth process and it appears that nitric oxide may be involved in opening potassium channels known as "K-Channels". L-arginine has been shown to promote natural growth hormone (GH) release from pituitary gland. GH has been shown to support a healthy lifestyle and may minimise a related decline. This material may also assist in kidney control of solubles in the body.

Insofar as colostrum in concerned, it is a material produced by nearly all mammals, by the mother of the offspring soon after birth. Medical research has shown that the most important immune and growth factors for human adults, children and animals can be provided by bovine colostrum. Because colostrum is a food rather than a drug it is free of toxicity and can be consumed without any known side effects. Colostrum research conducted by major medical centres and universities has shown clinically active bovine supplements derived from dairy cows naturally stimulates the nutrient-rich properties that a mother produces for her new-born offspring just after birth. Colostrum provides a supercharged blend of vital proteins, antibodies, anti-oxidants, immunoglobulin, growth factors, vitamins, minerals, enzymes and amino acids. The highly charged nature of colostrum precludes it being produced at sustained levels throughout the lactation of a mammalian parent. However, its initial production soon after parturition is provided by nature to give an early boost to the new born mammalian offspring. Colostrum is also believed to have the functional quality of combating and even reversing signs of aging.

In so far as Soy isoflavones are concerned, soy and most soy based products are believed to be the only plant food that has all the essential amino acids required of the human body, making it a "complete protein source". Soy foods generally do not have any cholesterol and most are high in fibre. In addition, soy has many vitamins, minerals and phyto-chemical compounds (like isoflavones) that work together to create numerous health benefits. Soy isoflavones are plant substances which are believe to contribute to hormonal balance when included as a dietary supplement. Soy products also include phytosterols. Soy isoflavones and phytosterols are known to supply mild estrogenic effects. The soy isoflavones, rich in phyto-nutrients, help prevent medic conditions associated with aging and from the large body of research can have a positive effect on hair for woman as well as for men. Soy beans contain phyto-estrogens, Genistein being one, which has been shown to have significant 5-alpha-reductase blocking activity, and androgen modulating activity. Another phyto-estrogen from soy beans, Daidzien, also helps block the 5-alpha-reductase enzyme. It is believed that this material may also reduce the risk of heart disease. Soy bean products have been shown to lower LDL ("Bad") cholesterol, and significantly increase HDL ("good") cholesterol.

Silica (horsetail herb) is believed to be the best and most concentrated plant source of the mineral silica for its introduction into the food chain. Silica is an important component of hair, nail, skin, bones, ligaments and collagen and is an essential herb needed for the physical integrity of these structures. Silica enhances the absorption of all minerals in the body. It has the effect of strengthening hair follicles and stimulates and increases growth of hair. Silica tends to decline as humans age. This decline can be responsible for many complaints associated with aging, and conditions have been linked to silica such as dry hair, hair loss, dry skin, weak brittle hair and nails, nervousness, poor energy levels and the like. Weak bone structure silica maximises the absorption of calcium by the bones, may be strengthened and taking horsetail has been clinically shown to help fractured and broken bones heal more quickly. Grains and cereal produced by modern fanning practices tend to be depleted of nutrients and silica. It is believed that very few foods have a high enough silica content to supply human dietary needs. Horsetail is rich silicic acid and silicates which provide approximately 2-3% elemental silicone. The high concentration of silica in horsetail is highly absorbable and utilised to facilitate calcium absorption, thereby promoting hair and bone growth and collagen formation. The herb also contains potassium, aluminium, manganese, calcium and 15 types of bioflavonoid. Horsetail also supports the skeletal system strengthening bones and connective tissues. Silicic acid contained in horsetail is believed to help improve circulation and build the immune nervous systems.

The nutrient inositol is believed to be essential for keratinocyte, the cells which line the hair follicles and produce hair. Inositol is an essential component of the b vitamin group and is often referred to as Vitamin B8. Hair loss often occurs when the diet is inadequate in B Vitamins—especially vitamin B6, inositol, biotin and folic acid, and the minerals sulphur and zinc. The B group vitamins, especially inositol, B5 (pantothenic acid) and B3 (niacin or nicotinamide) are especially important for hair growth. In the field of nutrition, well-being and health, inositol has an important part to play, not only being required for optimal general help, but also has specific functions in the body in which it assists. Examples of these functions include hair growth, calming effect, lowering cholesterol and lecithin. The body inositol levels can be depleted by caffeine, sulfonamide and excess water. Inositol is found in lecithin, whole grains, citrus fruit, liver, brewers yeast, vegetables, black strap molasses, soy beans and the like. The B group vitamins are important factors for proper maintenance of the nervous system, proper functioning of the cell and its energy metabolism. Any kind of mental and physical stress as well as poor eating habits greatly increase the bodies need for B group vitamins. Since B group vitamins are water soluble, they are not stored and must be supplied as the body needs them on a regular basis. Inositol is also believed to be a hydroxyl radical, and is believed to be essential for overall growth and preventing the thinning and greying of hair associating with aging.

Zinc is an essential mineral for body metabolism and has a myriad of health benefits for the human body. As far as the hair and scalp are concerned, it has been shown that zinc in high concentrations could completing inhibit the 5-alpha-reductase activity and that the vitamin B6 potentiated the inhibitory effect of zinc. Zinc is believed to stimulate the activity of approximately 100 enzymes, substances which promote biochemical reactions in the body. Zinc supports normal growth and a healthy immune system. The mineral also helps to protect cells against oxidative damage, safeguard red blood cell membranes against oxidative effects against of other minerals such as copper and iron, keeps cell membrane contents in place and selectively allows salts and other components to flow in and out of cells. Zinc is present in such foods as beans, whole grains, shellfish, red meat, dark meat, poultry and the like.

Vitamin E has been shown to retard cellular aging due to oxidation, the effect of maintaining peripheral circulation, is one of the more important anti oxidants, the strong presence of vitamin E being linked to longevity, reducing the effects of oxidated stress, and is a vital part of the formula involved in retarding cellular aging. Vitamin E is a natural detoxifier of impurities within the metabolic system of the body. It increases blood circulation for healthy hair growth but, as it cant be stored in the body, deficiencies can occur without a person being aware of it. It is essential for the body growth of body tissue cells and blood vessels. Longer living humans have been found to have higher amounts of vitamin E in their brain tissues.

Each member of the B vitamin group has a unique structure and performs a unique function in the human body. Vitamins B1, B2, B3 and biotin participate in different aspects of energy production, vitamin B6 is essential for amino acid, metabolism, and folic acid facilitates steps required for cell division. Each of these vitamins has many additional functions. Biotin is believed to increase elasticity of the hairs cortex preventing breakage and also thickens actual hair cuticle providing a fuller appearance and sounder result as a result of the increase diameter of the hair shaft. Biotin is sometimes referred to as Vitamin H, however it is generally accepted as being one of the B group vitamins. The vitamin promotes hair growth, protects against dryness, is involved in bio synthesis of unsaturated fats and is needed for energy metabolism. Folic acid is a water soluble B complex vitamin which assist with hair and tissue growth and cell functions. Para aminobenzoic acid is one of the lesser known members of the B complex family. It has been shown to be an anti grey hair vitamin. The vitamin has been shown to restore normal hair colour, and other research indicates this can also be done when combined with folic acid. This substance is commonly used in sunscreens. In so far as the other vitamin B's are concerned, Vitamin B1 (thiamine) has a role in the development of blood cells and the maintenance of hair and scalp and muscle tissue. Vitamin B2 (riboflavin) is involved in energy metabolism, and supports vision, hair and skin health. Vitamin B3 (niacin) is essential for the metabolism of carbohydrates, fat and alcohol, it helps maintain skin health and support the nervous and digestive systems. Pantothenic acid is considered to be important to the health of the skin and scalp, is necessary for the well being of every body cell and neither carbohydrate nor fat can be changed into energy without it. This nutrient is obtained from liver, kidney, egg yolks, whole grains, milk and potatoes. The combined effects of the materials used to formulate the formulation of the present invention are believed to provide trichological benefits effects in stopping and preventing dihydrotestosterone, the cause of hair loss and hair thinning in men and woman, as well as other effects. *Panax quinquefolium* root extract is also known by some as ginseng, a traditional herbal remedy from Asia, and used extensively in Asian cultures.

Although the invention has been described with reference to specific examples, it will be appreciated by persons skilled in the art that the invention may be embodied in other forms which are encompassed within the broad scope and ambit of the invention as herein set forth.

The invention claimed is:

1. An orally administrable formulation for treating hair loss or hair thinning, said formulation comprising:
   methylsulfonylmethane;
   beta-sitosterol;
   an extract from *Polygonum multiflorum*;
   an extract from *Ginkgo biloba*;
   an extract from *Equisetum arvense*;
   an extract from *Panax quinquefolium*;
   an isoflavone;
   arginine;
   vitamin B3;
   vitamin B5;
   vitamin B6;
   vitamin B7;
   vitamin B8;
   vitamin E;
   zinc; and
   colostrum.

2. A method of treating treating hair loss or hair thinning, or improving hair growth in an individual in need thereof, the method comprising administering to the individual the formulation of claims 1.

* * * * *